US009375235B2

(12) United States Patent
Swanstrom

(10) Patent No.: US 9,375,235 B2
(45) Date of Patent: Jun. 28, 2016

(54) METHOD AND SYSTEM FOR TRANSHIATAL ESOPHAGECTOMY

(71) Applicant: BOSTON SCIENTIFIC SCIMED, INC., Maple Grove, MN (US)

(72) Inventor: Lee L. Swanstrom, Portland, OR (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 57 days.

(21) Appl. No.: 14/103,493

(22) Filed: Dec. 11, 2013

(65) Prior Publication Data

US 2014/0163318 A1   Jun. 12, 2014

Related U.S. Application Data

(60) Provisional application No. 61/736,121, filed on Dec. 12, 2012.

(51) Int. Cl.
| | |
|---|---|
| A61B 17/34 | (2006.01) |
| A61B 1/018 | (2006.01) |
| A61B 17/28 | (2006.01) |
| A61B 17/3205 | (2006.01) |
| A61B 1/00 | (2006.01) |
| A61B 17/29 | (2006.01) |
| A61B 17/00 | (2006.01) |

(52) U.S. Cl.
CPC ............... *A61B 17/34* (2013.01); *A61B 1/018* (2013.01); *A61B 17/3431* (2013.01); *A61B 1/00154* (2013.01); *A61B 17/28* (2013.01); *A61B 17/29* (2013.01); *A61B 17/3205* (2013.01); *A61B 2017/003* (2013.01); *A61B 2017/2906* (2013.01); *A61B 2017/3445* (2013.01)

(58) Field of Classification Search
CPC ........... A61B 2017/1789; A61B 1/018; A61B 1/273; A61B 17/0281; A61B 17/34; A61B 2017/3445; A61B 17/3431
See application file for complete search history.

(56) References Cited

U.S. PATENT DOCUMENTS

| | | | | |
|---|---|---|---|---|
| 8,715,270 | B2 * | 5/2014 | Weitzner | A61B 1/0014 600/111 |
| 2010/0312048 | A1 * | 12/2010 | Forsell | A61B 17/0469 600/37 |

\* cited by examiner

*Primary Examiner* — Howie Matthews
(74) *Attorney, Agent, or Firm* — Bookoff McAndrews, PLLC

(57) ABSTRACT

Embodiments include a method of performing a medical procedure in a patient. The method includes creating an incision in an abdominal wall of the patient, inserting a flexible guide tube into the incision, and advancing a flexible instrument through the guide tube. The method also includes positioning a distal tip of the guide tube adjacent to a gastroesophageal junction and passing the instrument through an esophageal hiatus.

20 Claims, 15 Drawing Sheets

METHOD AND SYSTEM FOR TRANSHIATAL ESOPHAGECTOMY

CROSS-REFERENCE TO RELATED APPLICATIONS

This application claims the benefit of priority from U.S. Provisional Application No. 61/736,121, filed on Dec. 12, 2012, the entirety of which is incorporated by reference herein.

FIELD

Embodiments of the present invention generally relate to medical devices. Specifically, embodiments of the present invention relate to systems and devices for use during surgical procedures, such as, a transhiatal esophagectomy. Embodiments of the present invention also encompass related procedures.

BACKGROUND

It is generally desirable to minimize the invasiveness of medical procedures, including therapeutic or diagnostic procedures. Invasive "open" medical procedures are generally more expensive than minimally invasive "keyhole" procedures, and there is often a greater risk of complication and discomfort for the patient. Since open surgery typically requires relatively large incisions, blood loss can be high and the risk of infection or other post-operative complications may increase. Large incisions may require extended recovery times to heal and leave unsightly scarring. Accordingly, methods, systems, and devices that reduce trauma to the patient, are less invasive, or enhance recovery are desirable.

Numerous minimally invasive procedures have been developed, including some that use laparoscopic devices. However, laparoscopic devices are rigid and must be pivoted about the incision through which they are passed. Precise control of the distal end of a rigid laparoscopic device can be difficult due to this pivoting movement. Visualization may also be complicated because a separate optical device is required. In addition to requiring an extra incision, the optical device must be appropriately positioned to provide a useful field of view of the surgical site. Maintaining or adjusting the optical device relative to the laparoscopic device is time consuming and may involve constant attention, especially if the surgical site is moved during the procedure. Moreover, controlling the ends of multiple laparoscopic devices based on a point of view well proximal to the surgical site is complicated, requires extensive training, and may result in unwanted trauma to surrounding tissue. Robotic systems that use rigid instruments suffer similar disadvantages.

One region that is particularly difficult to access using standard rigid laparoscopic devices is the mediastinum. Thoracic access is limited by the surrounding ribs and sternum, and abdominal access places the incision at considerable distance from the desired surgical site. Abdominal laparoscopic access to mediastinal tissue poses significant ergonomic challenges, including working in small spaces with insufficient triangulation or visualization. Dissection around the hilum of the lung is essentially performed blind, which may affect oncologic resection or long term prognosis. Inadvertent injuries to the surrounding vital structures may also result. The difficulties associated with mediastinal access have hindered the development of esophagectomy procedures using laparoscopic devices.

Standard endoscopic devices are also unsuitable for accessing the mediastinum or performing esophagectomies because, in part, because the approach is not through a natural body cavity. Standard endoscopes are specifically designed to flex to pass through the lower gastrointestinal tract or the esophagus. Consequently, they are not configured for use in procedures requiring navigation past organs or through tissue without surrounding support structure to guide them. Standard endoscopic devices are too long or too flexible for such navigation. In addition, these devices are not configured for ergonomic control of instruments passed through them. Control of a standard endoscopic device often requires two hands to operate, meaning that only one device can be operated at a time by a surgeon. Nor can standard endoscopic devices be locked or moved incrementally relative to a patient. The present disclosure overcomes at least some of the limitations of prior art.

It is to be understood that both the foregoing general description and the following detailed description are exemplary and explanatory only and are not restrictive of the invention.

SUMMARY

In one aspect, a method of performing a medical procedure in a patient includes creating an incision in an abdominal wall of the patient, inserting a flexible guide tube into the incision, and advancing a flexible instrument through the guide tube. The method also includes positioning a distal tip of the guide tube adjacent to a gastroesophageal junction and passing the instrument through an esophageal hiatus.

In another aspect, a method of performing a medical procedure in a patient includes creating an incision in the patient, passing a distal tip of a flexible guide tube through the incision, locating a flexible optical device and a flexible instrument within the guide tube, and retracting at least part of an organ to create a pathway from the incision to an esophageal hiatus. The method also includes advancing the distal tip of the guide tube along the pathway to the esophageal hiatus, positioning the optical device to visualize a phrenoesophageal ligament, dividing the phrenoesophageal ligament using the instrument, and passing at least one of the guide tube, the optical device, and the instrument through the esophageal hiatus.

In a further aspect, a method of performing a medical procedure in a patient includes creating an incision in an umbilicus of the patient, passing a distal end of a flexible guide tube and a distal end of a flexible instrument through the incision, and creating a pathway from the incision to an esophageal hiatus using at least one of the guide tube and the instrument. The method also includes positioning an optical device to visualize the esophageal hiatus, dilating the esophageal hiatus using the instrument, and passing the instrument through the esophageal hiatus and into a mediastinum.

Additional objects and advantages of the invention will be set forth in part in the description which follows, and in part will be obvious from the description, or may be learned by practice of the invention. The objects and advantages of the invention will be realized and attained by means of the elements and combinations particularly pointed out below.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

The terms "proximal" and "distal" are used herein to refer to the relative positions of the components of the exemplary endoscopic system 10. When used herein, "proximal" refers to a position relatively closer to the exterior of the body or closer to the surgeon using endoscopic system 10. In contrast, "distal" refers to a position relatively further away from the surgeon using endoscopic system 10 or closer to the interior of the body.

Figure 1A:
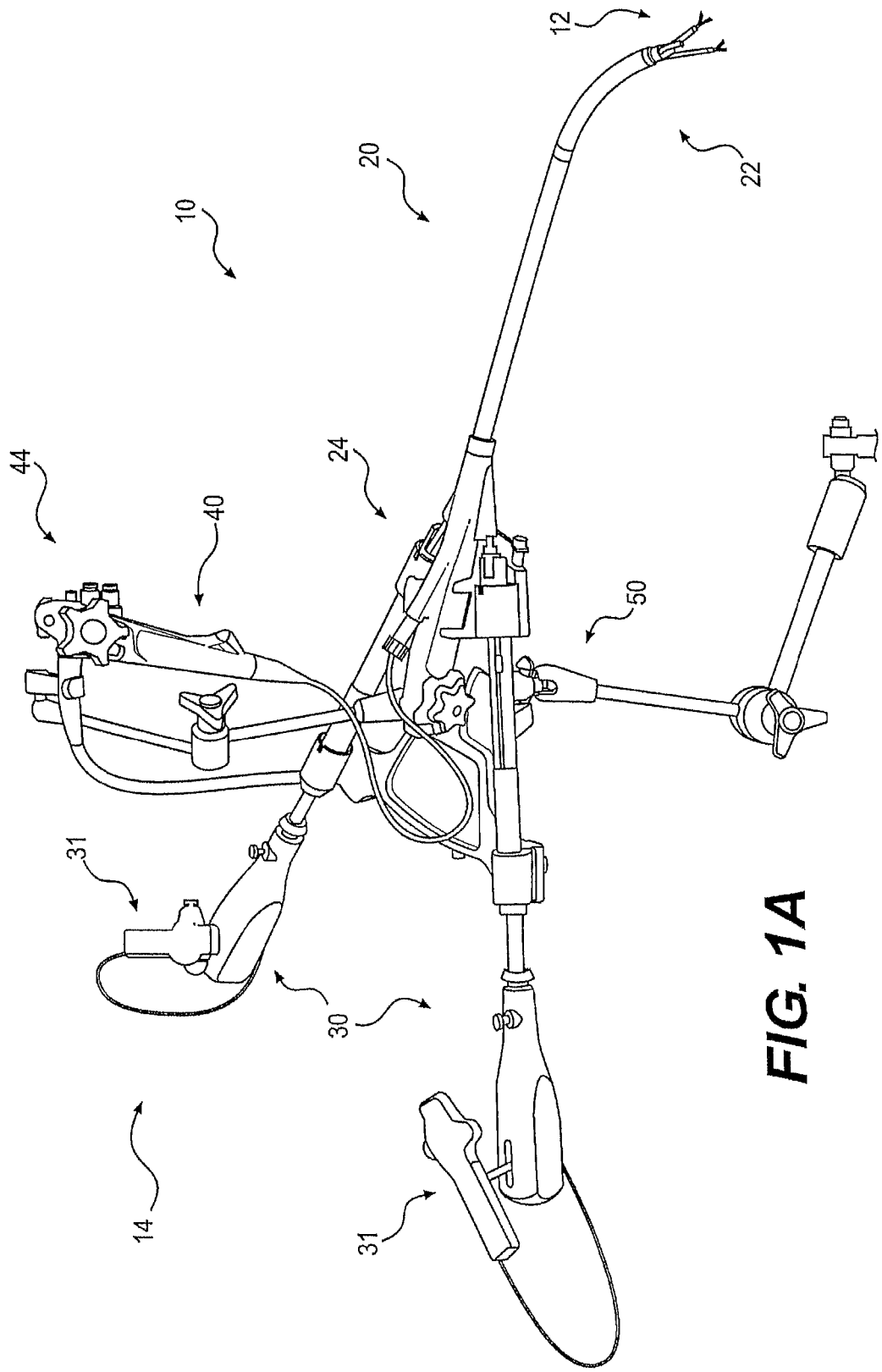
FIG. 1A is a perspective view of an endoscopic system, according to an exemplary embodiment.

FIG. 1A depicts an endoscopic system 10, according to an exemplary embodiment. Endoscopic system 10 can include a direct drive endoscopic system (DDES), and may be used for a therapeutic or a diagnostic procedure. Such procedures may be performed by inserting an endoscopic device, guide tube, catheter, or other medical device into the body through an anatomic opening (e.g., an incision or a natural orifice).

Although in the description that follows, endoscopic system 10 is described and shown as being inserted into the body through an incision in an abdominal wall of a patient, it should be emphasized that this description is exemplary only. For example, endoscopic system 10 may also be used for procedures in or near other body organs, such as stomach, intestine, pelvic area, bladder, or other organs in the mediastinum or abdominal cavity. Embodiments of the current disclosure may be used in, but are not limited to, single incision laparoscopic surgical (SILS) procedures or natural orifice transluminal endoscopic surgery (NOTES) procedures.

Figure 1B:
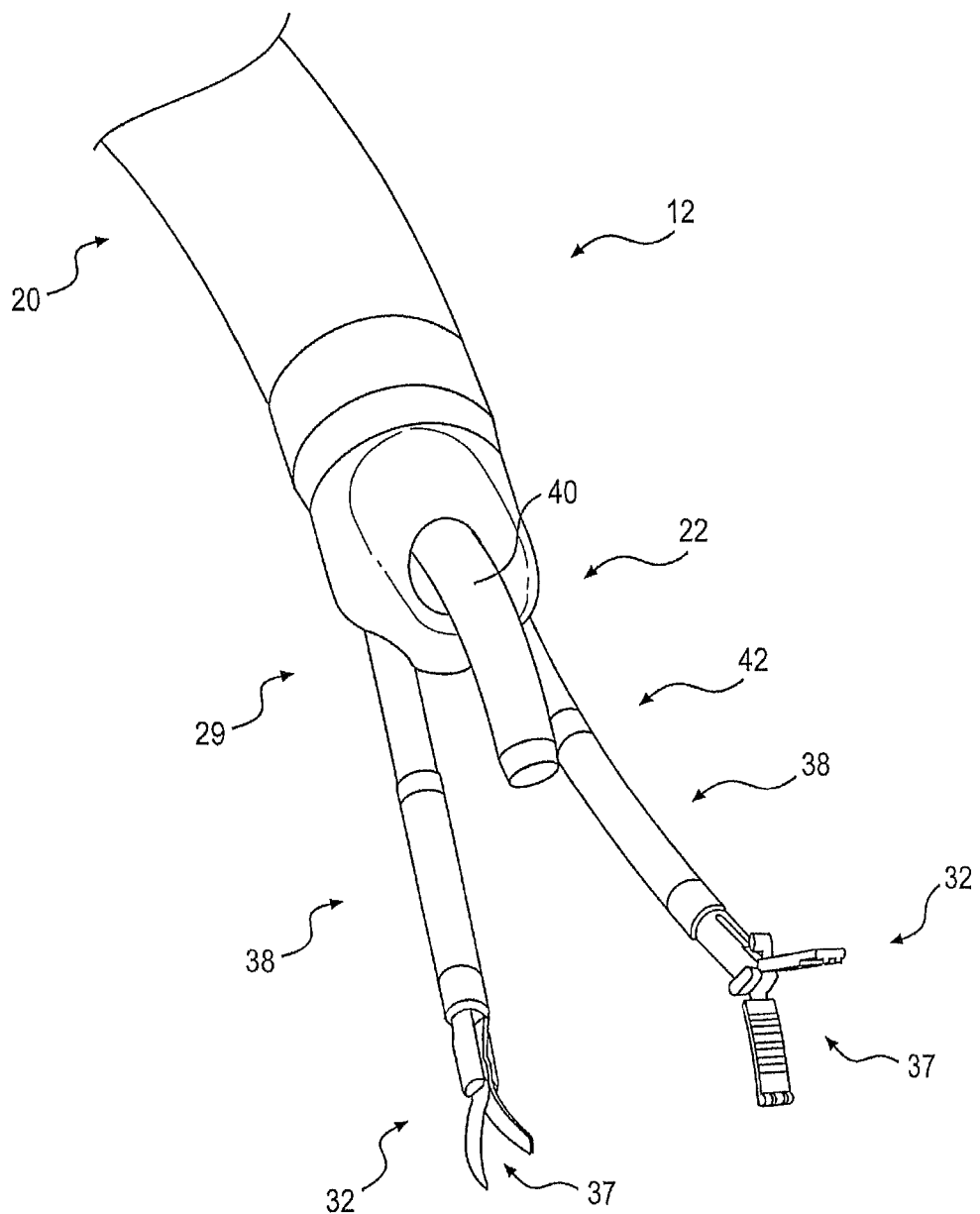
FIG. 1B is an enlarged perspective view of a distal region of the endoscopic system shown in FIG. 1A, according to an exemplary embodiment.

According to an exemplary embodiment, endoscopic system 10 may include a guide tube 20, one or more instruments 30, an optical device 40, and a platform 50. A distal region 12 of endoscopic system 10 may be inserted into a patient to perform various medical procedures as described herein. During these procedures, a proximal region 14 of endoscopic system 10 remains outside the patient and is manipulated by a surgeon to control components of distal region 12, as shown in FIG. 1B.

Endoscopic system 10 is configured to permit a surgeon to operate two instruments 30 simultaneously. In other embodiments, the surgeon may operate one instrument 30 while moving platform 50 or adjusting optical device 40. Generally, platform 50 and guide tube 20 are configured to permit simultaneous and independent operation of two instruments 30 using one hand on each instrument 30. Platform 50 can be rigidly coupled to an operating table, and thus be fixed relative to a patient during an operation. Platform 50 can also be locked and unlocked to permit movement relative to the operating table or patient.

Guide tube 20 and optical device 40 can be removably coupled to platform 50. Optical device 40 can include a commercially available endoscope or other imaging device. Other features and operations of the various components of endoscopic system 10 will be described below. Some exemplary embodiments of guide tube 20, instrument 30, optical device 40, and platform 50 (frame) are disclosed, for example, in U.S. patent application Ser. No. 11/946,790, entitled "Multi-Part Instrument Systems and Methods," which is hereby incorporated by reference in its entirety.

Figure 2:
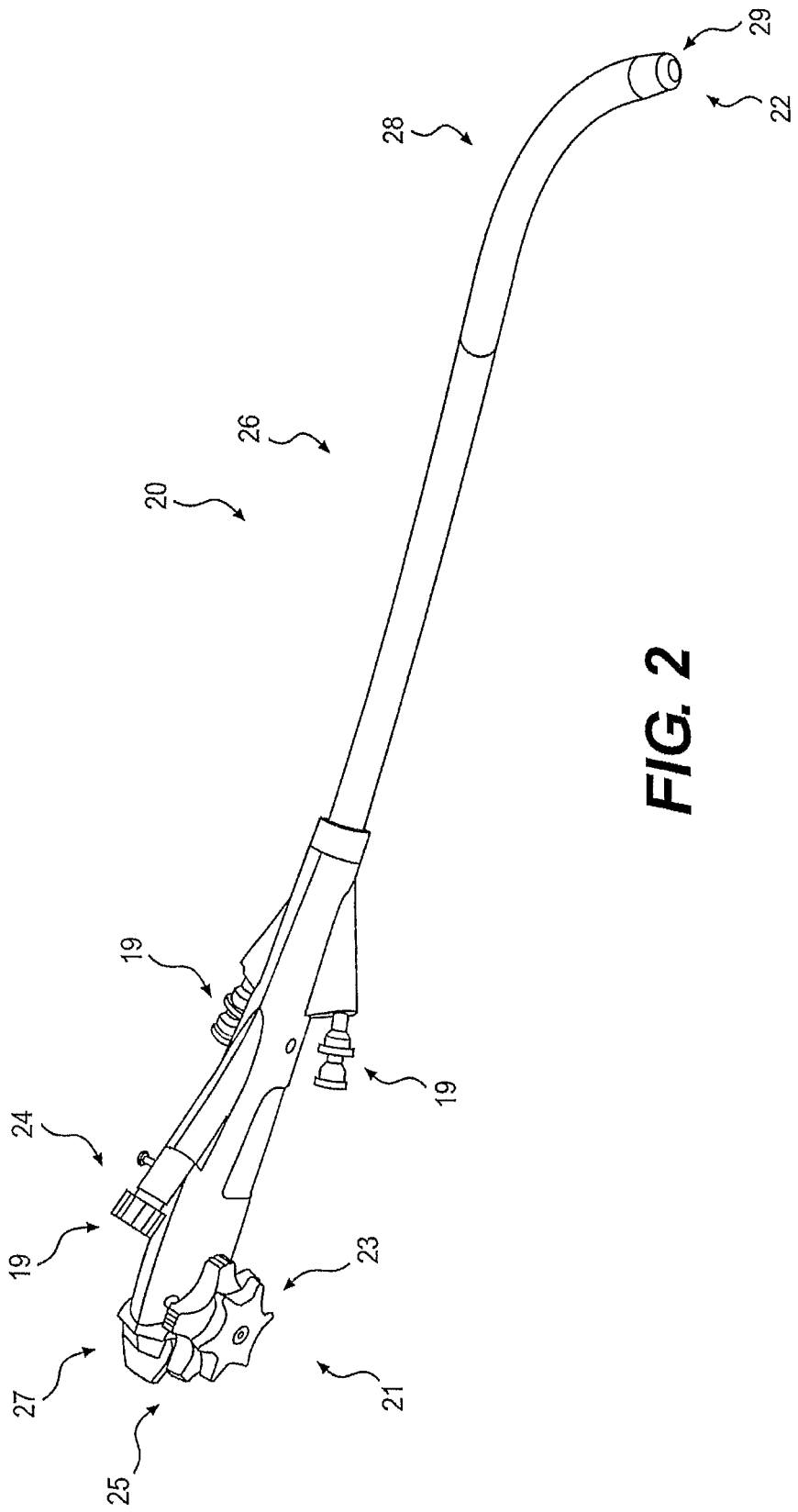
FIG. 2 is a perspective view of a guide tube, according to an exemplary embodiment.

As shown in FIG. 2, guide tube 20 may include a proximal region 24 housing one or more ports 19 configured to receive one or more instruments 30 or optical devices 40. Lumens (not shown) may extend longitudinally (axially) between ports 19 and a distal region 22 of guide tube 20. In other embodiments, guide tube 20 can include integrated optics (not shown), such as, for example, a light source, wave guide, imaging chip, or other similar components.

Guide tube 20 may include a region 26 and an articulating region 28. Region 26 can be flexible enough to bend around organs yet rigid enough to adequately transfer compressive force from proximal region 24 to distal region 22. For example, region 26 could be configured to bend to allow distal region 22 to be navigated from an incision in the umbilicus to an inferior surface of the diaphragm. Such navigation requires sufficient flexibility to flex in order to pass around organs in the abdominal cavity and sufficient rigidity to force distal region 22 through connective tissue supporting the abdominal organs.

Articulating region 28 may be controllably moved via a control mechanism 21 located at proximal region 24. For example, a first knob 23 could be rotated to move articulating region 28 left and right while a second knob 25 could be rotated to move articulating region 28 up and down. A brake 27 can be configured to lock or unlock the movement of articulating region 28. Controlled movement of articulating region 28 can control movement of distal region 22 of guide tube 20, a distal region 32 of instrument 30, or a distal region 42 of optical device 40 relative to a patient.

FIG. 1B shows distal region 12 of endoscopic system 10, according to an exemplary embodiment. Specifically, distal region 42 of optical device 40 is shown extended from distal region 22 of guide tube 20. Likewise, two instruments 30 are shown with their distal ends 32 extended from distal region 22. One or more instruments 30 or optical device 40 may be advanced from, or retracted into, distal region 22. Distal region 22 can include a rounded distal tip 29 configured to aid passage of guide tube 20 through tissue.

Optical device 40 can be moved relative to guide tube 20 to adjust a viewing angle, viewing distance, or location of distal end 42 relative to the patient or the surgical site. In some embodiments, an articulating region (not shown) can be configured to permit movement and repositioning of distal end 42 via movement of various controls located at a proximal region 44 of optical device 40 (FIG. 1A). Optical device 40 may be independently moveable with respect to guide tube 20 or instrument 30. For example, optical device 40 may be moveably received in a lumen in guide tube 20, as shown in FIG. 1B. The surgeon may move optical device 40 longitudinally, laterally, or rotationally to control the position of distal end 42 with respect to guide tube 20. Distal end 42 of optical device 40 may also be positioned with respect to instrument 30 so that optical device 40 provides a "bird's eye view" of the surgical site or end effectors 37 of instruments 30.

In some embodiments, optical device 40 may be embedded into or attached to guide tube 20 or instrument 30. For example, optical device 40 may be on a distal-facing, circumferential, or other outer surface near distal ends 22, 32. With such an "integral" optical device 40, the surgeon may move guide tube 20 or instrument 30 longitudinally, laterally, or rotationally to control the position of optical device 40 with respect to the patient.

In use, distal end 32 of instrument 30 may be articulated by moving articulating region 38. For example, actuators 31 (shown in FIGS. 1A, 3) may be moved relative to instruments 30 to control up/down and left/right movement of articulating regions 38 similar to that described above for articulating region 28. The surgeon may move each instrument 30 longitudinally (e.g., in the distal and proximal directions, axially), laterally (e.g., side to side or up and down), or rotationally with respect to guide tube 20.

Figure 3:
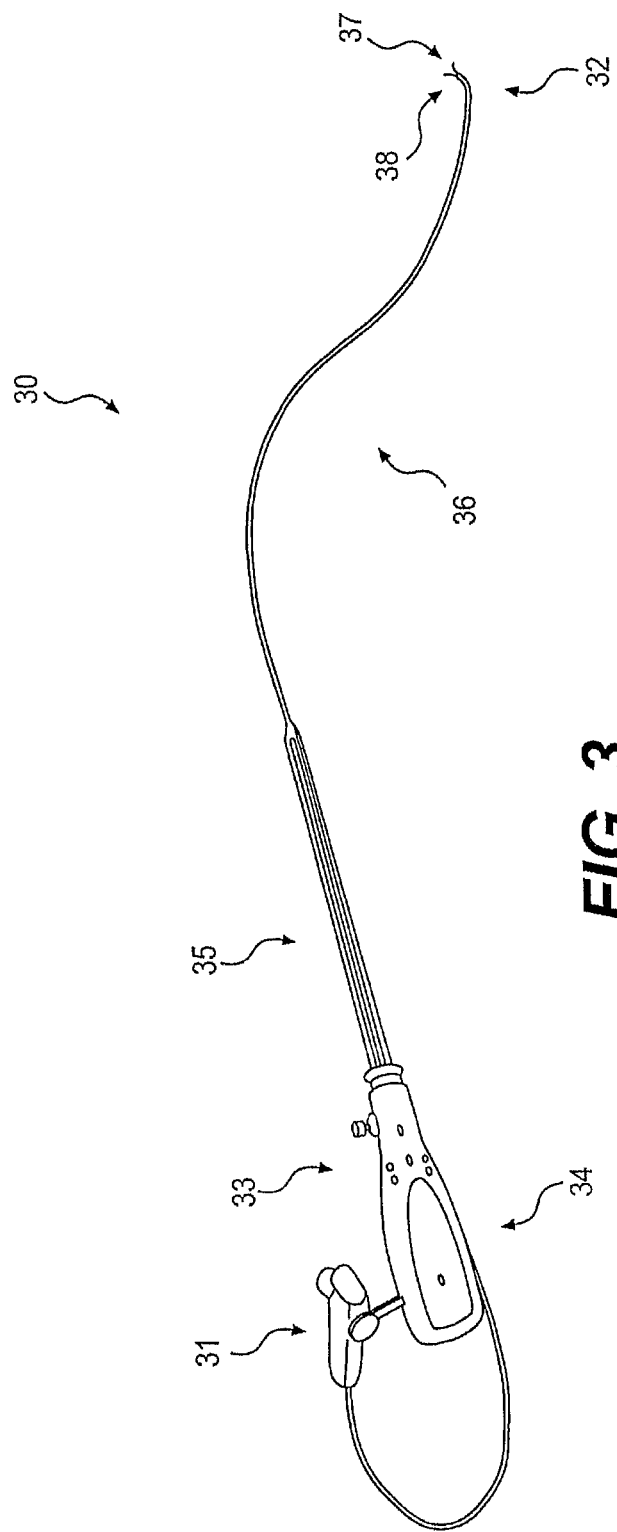
FIG. 3 is a perspective view of an instrument, according to an exemplary embodiment.

FIG. 3 shows a perspective view of instrument 30, according to an exemplary embodiment. Instrument 30 includes a proximal region 34 moveably coupled to actuator 31. Actuator 31 can be rotatably coupled to a controller body 33 such that rotation about two or more axes can control movement of articulating region 38. For example, actuator 31 can be rotated clockwise or anticlockwise to move articulating region 38 left and right. Actuator 31 can also be tilted forward or backwards relative to controller body 33 to move articulating region 38 up or down. Some exemplary embodiments of actuator 31 are disclosed, for example, in U.S. Pat. No. 8,057,462, entitled "Medical Device Control System," which is hereby incorporated by reference in its entirety.

Instrument 30 can also include rigid region 35 configured for placement in a bearing tube 53 (FIG. 5), as described below. Region 35 does not generally extend into guide tube 20, but is rather used as a bearing to support instrument 30 on platform 50. Instrument 30 also includes a flexible region 36 configured for placement within guide tube 20. Similar to guide tube 20, the structural properties of region 36 can also be varied to provide sufficient flexibility to maneuver around organs and sufficient rigidity to exert a dissecting force on tissue.

Each instrument 30 can also include end effector 37 located at distal region 32. Instrument 30 may include one or more control elements (not shown) connected to end effector 37 to allow the surgeon to control the movement of end effector 37. End effector 37 may be connected to articulating region 38 to allow end effector 37 to move up/down or left/right. Instrument 30 and end effector 37 may include a range of configurations for use with various medical procedures.

Figure 4A:
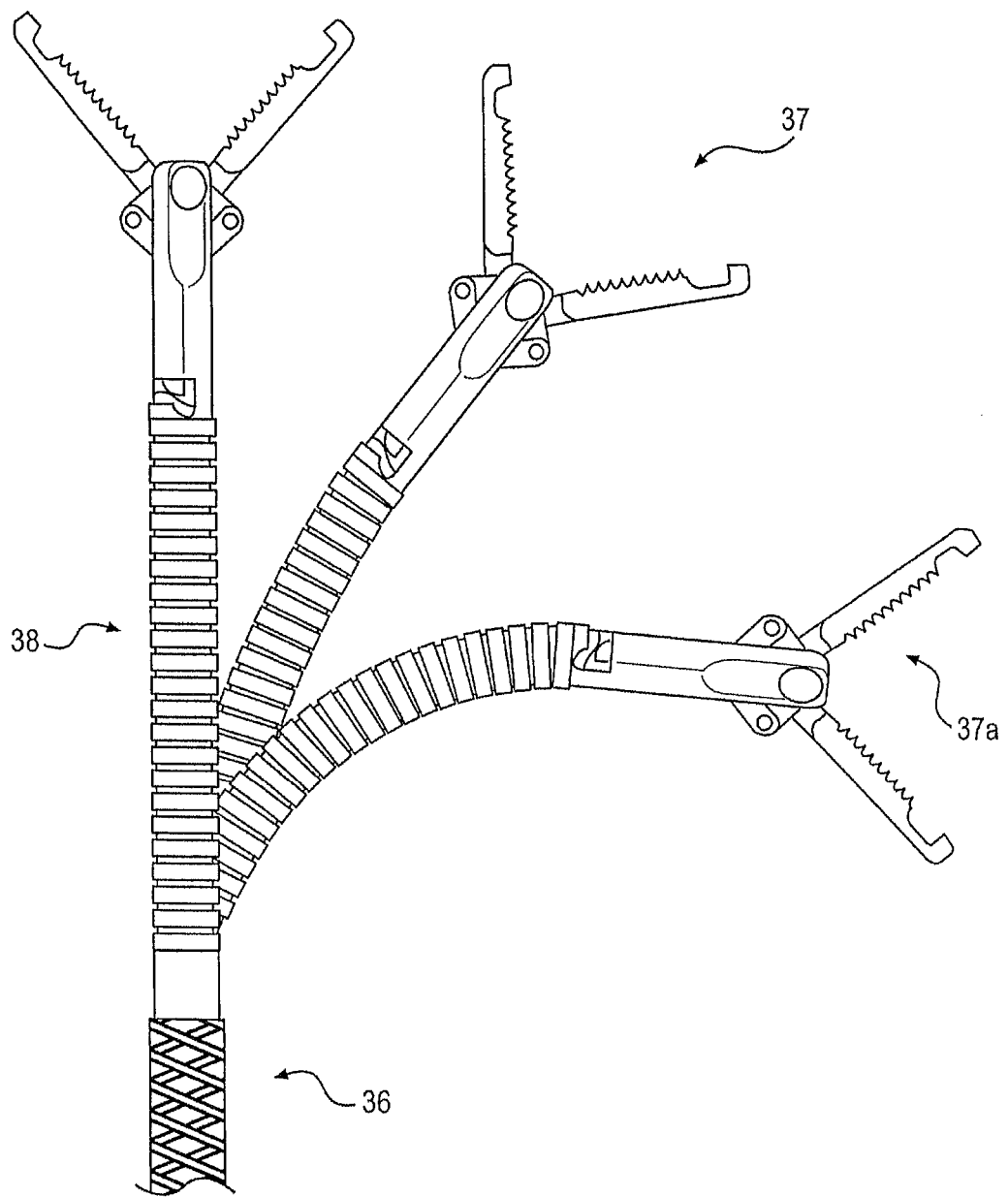
FIG. 4A is a side view of an instrument end effector showing articulation in three different positions, according to an exemplary embodiment.
Figure 4B:
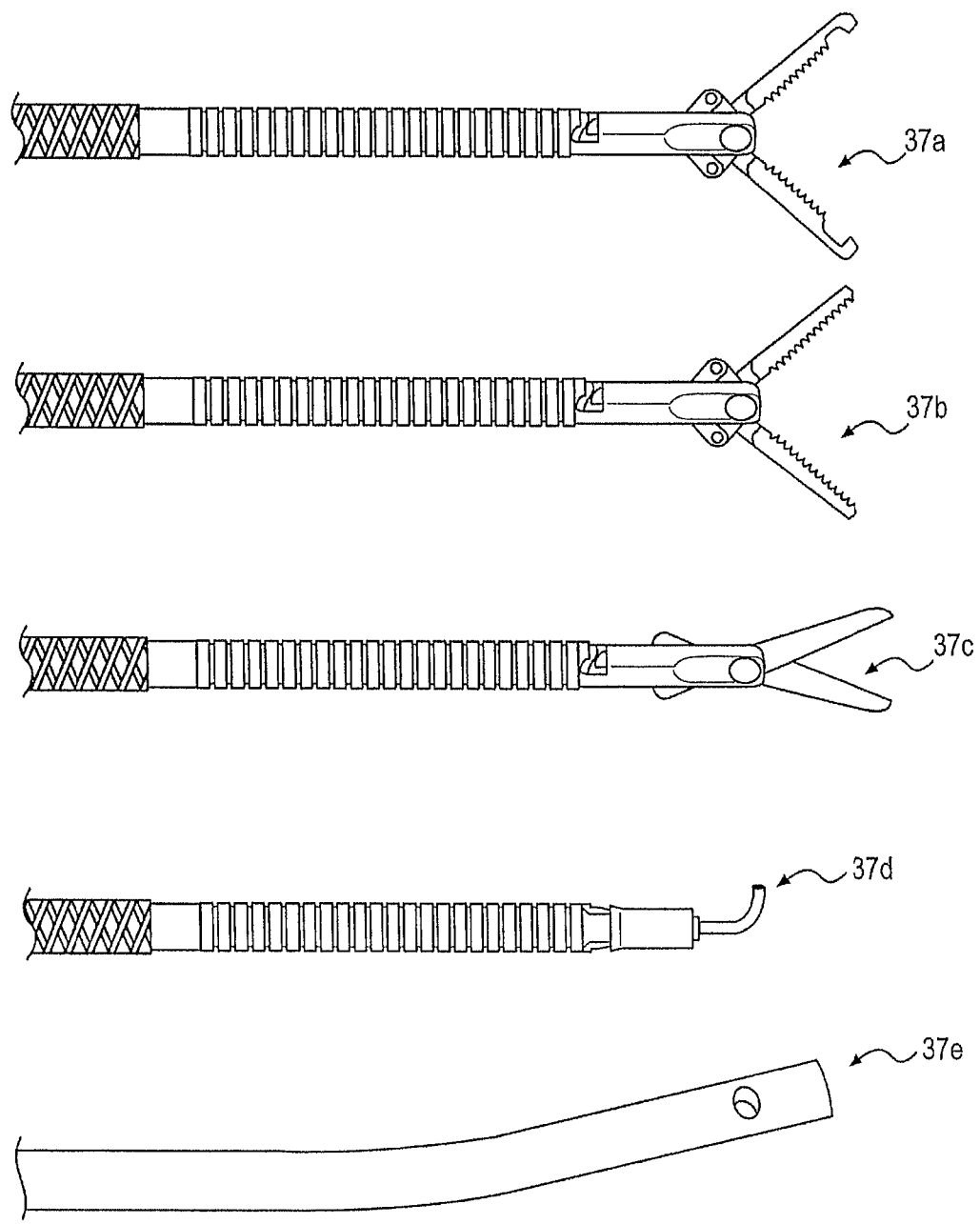
FIG. 4B is a side view of five instrument end effectors, according to exemplary embodiments.

FIGS. 4A, 4B show various end effectors 37 that may form part of instrument 30. End effector 37 may include a device configured to assist in performing a surgical procedure. FIG. 4A shows the movement of articulating region 38, including a grasper end effector 37a. Various other types of end effectors 37 are contemplated for use with instrument 30. Generally, end effector 37 may include, but is not limited to, a cutting device (e.g., scissors, tissue cutter, etc.), forceps, a fixation device, a manipulation device, a dissection device, a support device, a sealing device, a needle holder, a closure device (e.g., clips, staples, loops, ligator, suturing device, etc.), a retrieval device (e.g., snare, basket, loop, a fluid extraction device, etc.), a tissue exploration device (e.g., optical device, illumination device, etc.), a tissue sampling device, a delivery device, a device for aiding in the patency of a lumen or for dilating an opening (e.g., a balloon or other expandable member, patency brush, stent, fan retractor, wire structure, etc.), a grasping device, a stabilizing device, an ablation device, a resection device, a pressure application device, an energy delivery device, etc. Instrument 30 may include a blunt or rounded tip for exploration or for assisting another instrument 30 or end effector 37 (e.g., an obturator). For example, as shown in FIG. 4B, grasper 37a, a dissector 37b, a pair of scissors 37c, an electrosurgical device 37d, and a suction/irrigation tube 37e may be incorporated with instrument 30.

Figure 5:
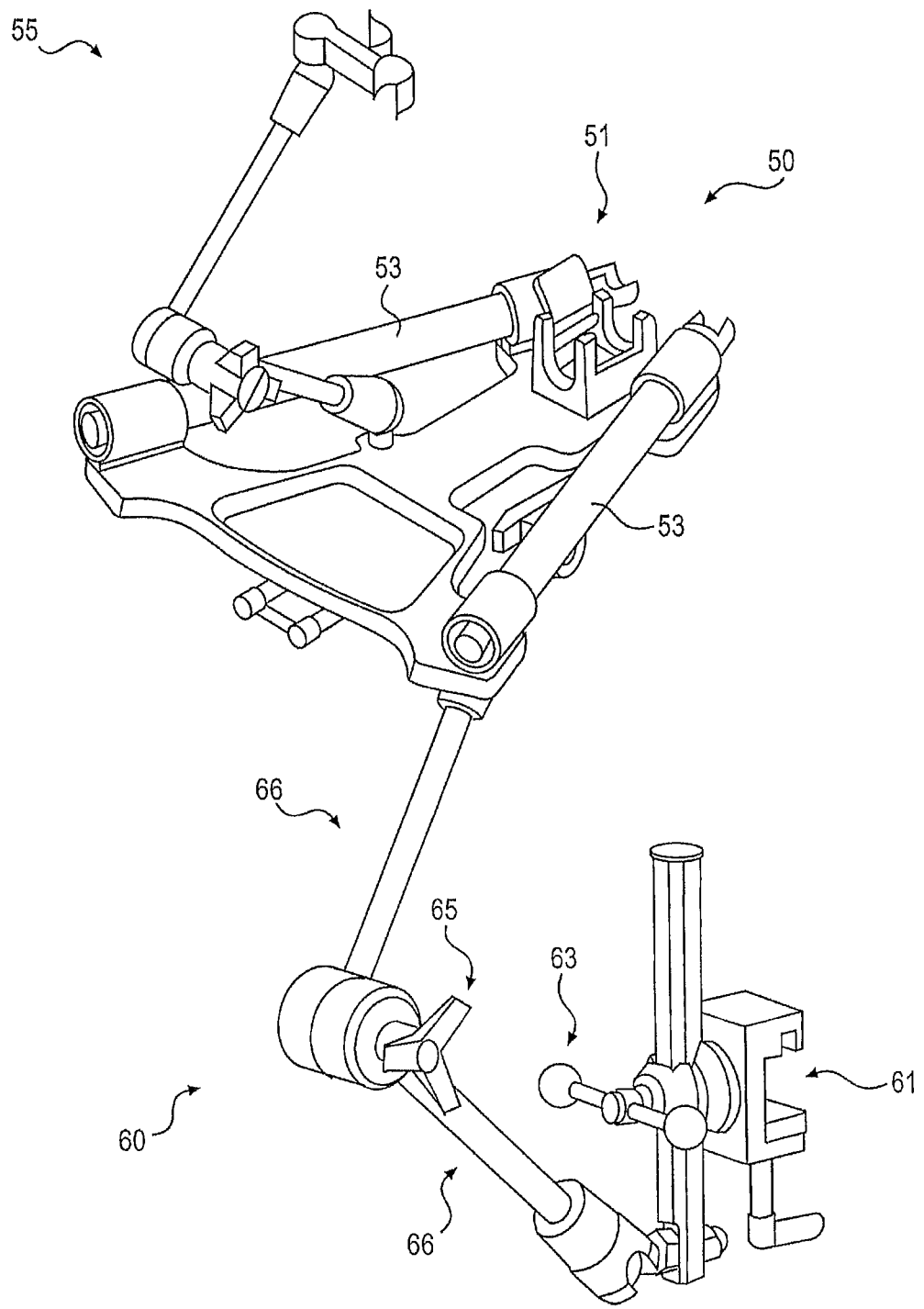
FIG. 5 is a perspective view of a platform, according to an exemplary embodiment.
Figure 6:
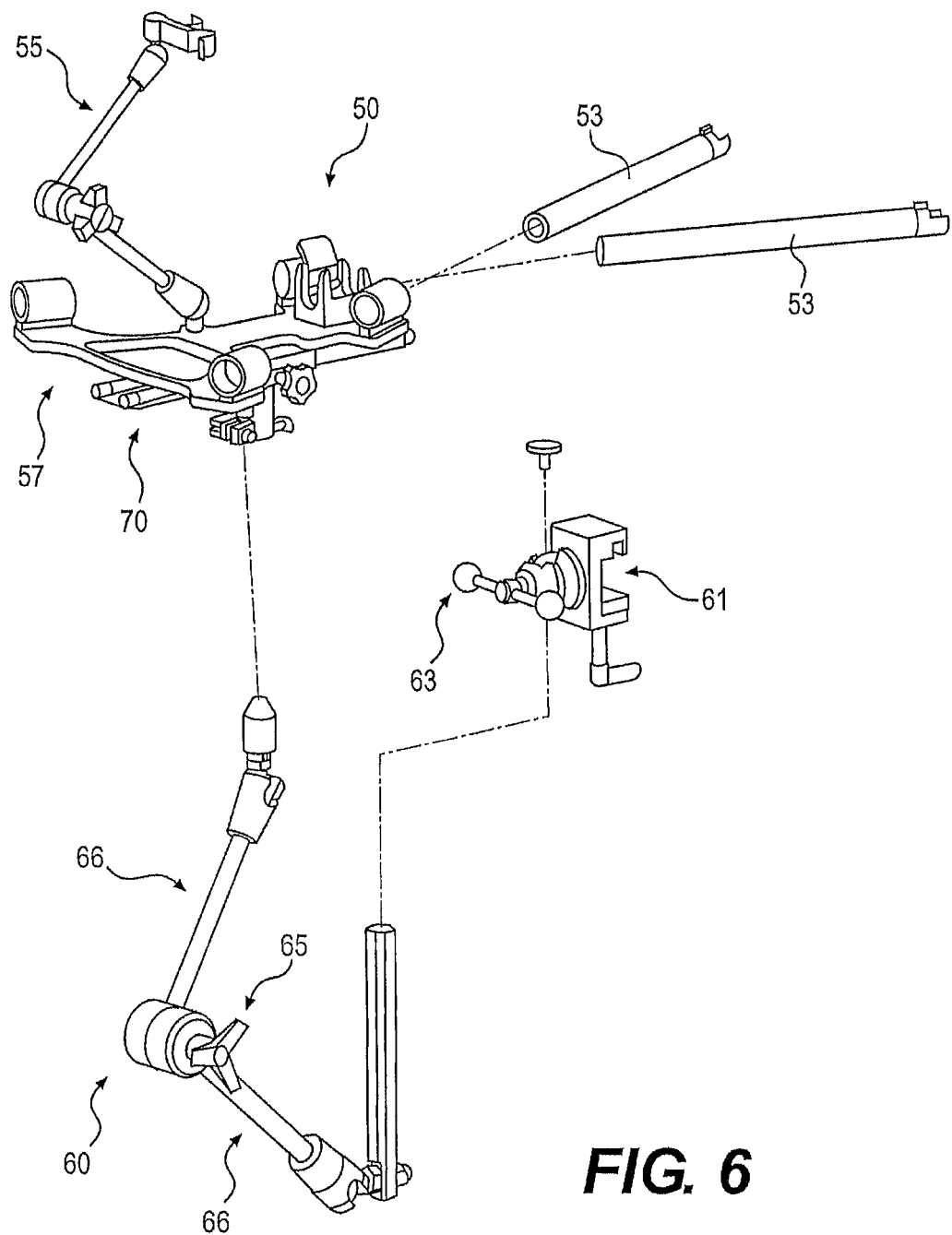
FIG. 6 is an exploded view of the platform shown in FIG. 5, according to an exemplary embodiment.

FIGS. 5 and 6 illustrate platform 50, according to an exemplary embodiment. As explained above, platform 50 can be attached to an operating table and configured to receive guide tube 20, one or more instruments 30, or optical device 40. Guide tube 20 can be fixedly mounted to platform 50 using a latch 51 or other attachment mechanism. Instrument 30 can be moveably coupled to platform 50 via bearing tube 53. Some exemplary embodiments of bearing tube 53 are disclosed, for example, in U.S. patent application Ser. No. 13/297,675, entitled "Bearing Assembly for Instrument," which is hereby incorporated by reference in its entirety. Optical device 40 can be moveably coupled to platform 50 via an arm 55.

Platform 50 can be mounted to an operating table (not shown) using a mounting system 60. Mounting system 60 can include a clamp 61 configured to releasably couple to the operating table. A lever 63 may mechanically engage clamp 61 to provide locking/unlocking of select movement between mounting system 60 and clamp 61. In other words, locking lever 63 would limit movement and unlocking lever 63 would permit free movement of platform 60 in one or more directions. Alternatively, lever 63 could be moved to incrementally move (e.g., raise or lower) mounting system 60, and hence endoscopic system 10, relative to the operating table.

In addition to, or instead of, controlling movement using lever 63, a knob 65 may mechanically engage one or more mounting arms 66 to lock or free movement between two or more mounting arms 66. Alternatively, knob 65 could be moved to incrementally move two or more mounting arms 66 relative to each other.

Figure 7A:
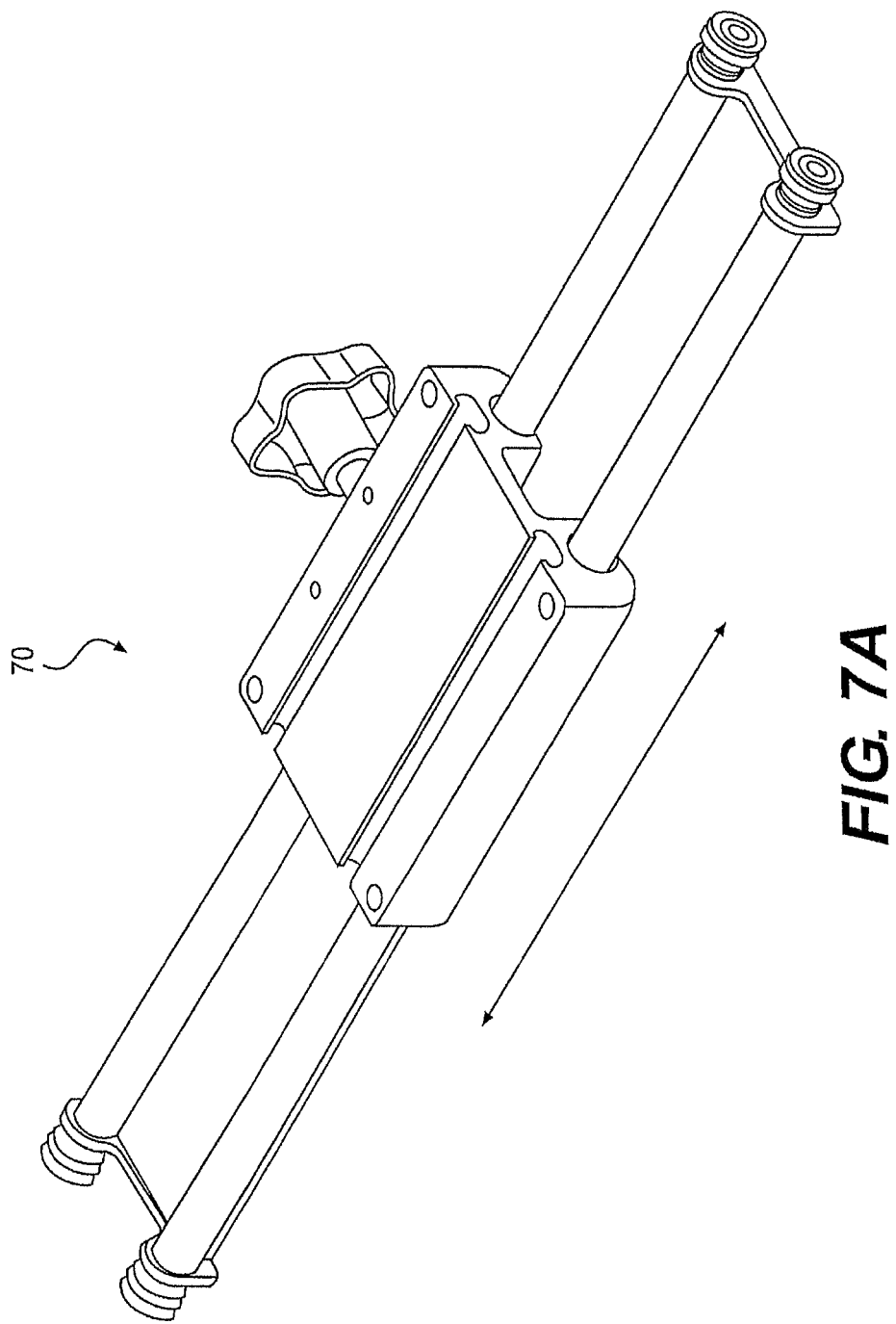
FIG. 7A is a perspective view of a slide assembly, according to an exemplary embodiment.
Figure 7B:
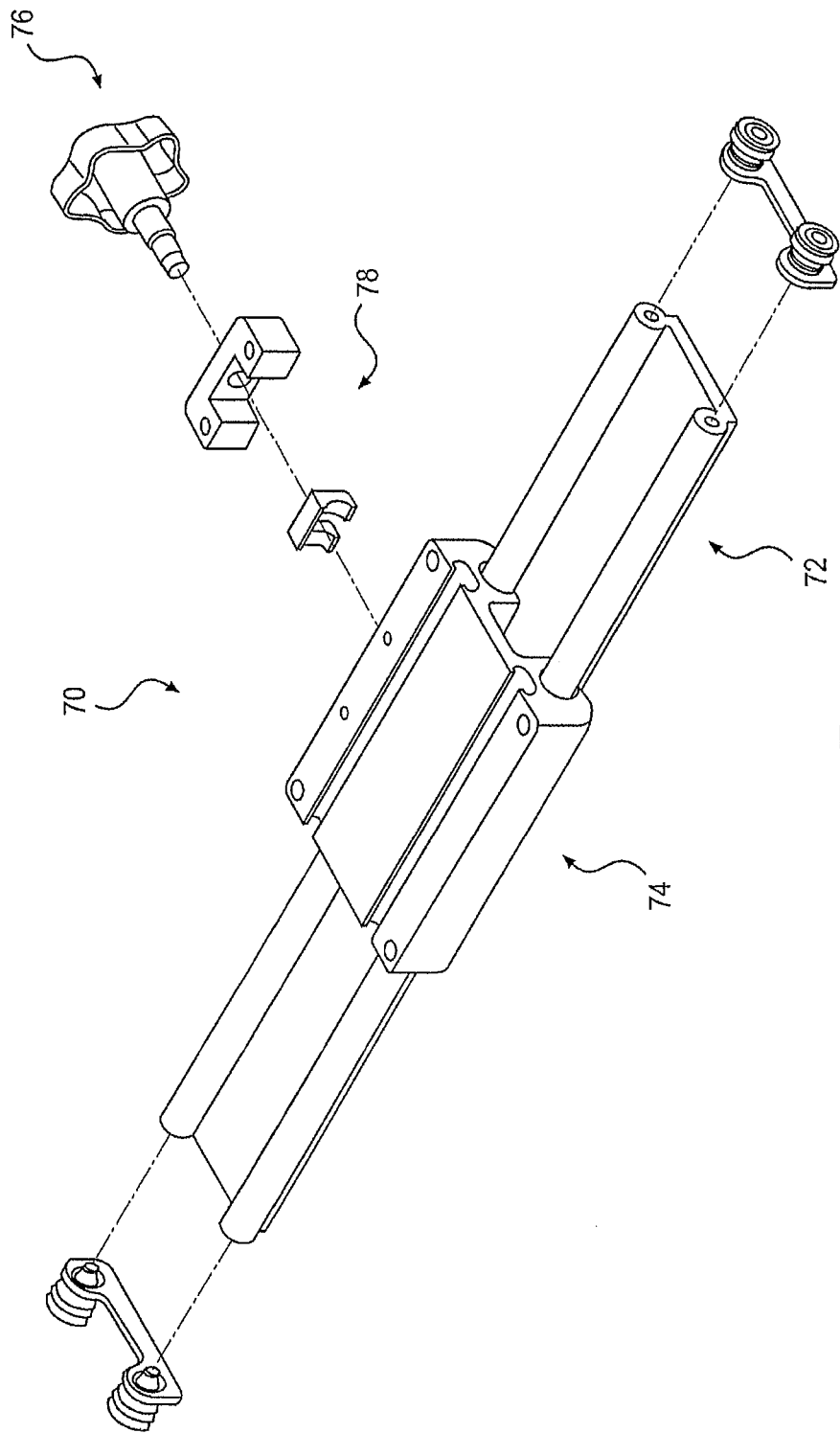
FIG. 7B is an exploded view of the slide assembly shown in FIG. 7A, according to an exemplary embodiment.

FIGS. 7A and 7B show a slide assembly 70, according to an exemplary embodiment. At least part of slide assembly 70 can be configured to move in one or more directions, as indicated by the double arrow in FIG. 7A. Slide assembly 70 can be located between mounting system 60 and a plate 57 of platform 50 (FIG. 6). Slide assembly 70 can include one or more rails 72 and a carriage 74 moveably coupled to the one or more rails 72. Plate 57 can be fixedly coupled to one or more rails 72 and carriage 74 can be fixedly coupled to mounting system 60. To control movement of carriage 74 relative to rails 72, slide assembly 70 can include a knob 76 and a mount 78 configured to couple knob 76 to carriage 74 or rails 72.

In use, knob 76 may mechanically engage carriage 74 or rails 72 to provide locking/unlocking of movement between carriage 74 and rails 72. Alternatively, knob 76 could be moved to incrementally translate carriage 74 relative to rails 72. As explained above with respect to mounting system 60, slide assembly 70 can be used to selectively move guide tube 20 relative to the operating table.

Various combinations of one or more levers 63, knobs 65, 76 or other devices could be used to provide select movement of endoscopic system 10 relative to the patient. In other embodiments, endoscopic system 10 can include a gear, belt, pulley, or other type of drive system configured to provide selective movement. For example, various components of endoscopic system 10 could be configured for locking/unlocking, incremental, or other types of select movement. Select movement of one or more components of endoscopic system 10 can provide advantages to a surgeon performing a procedure on a patient's organ, as described herein.

Figure 8:
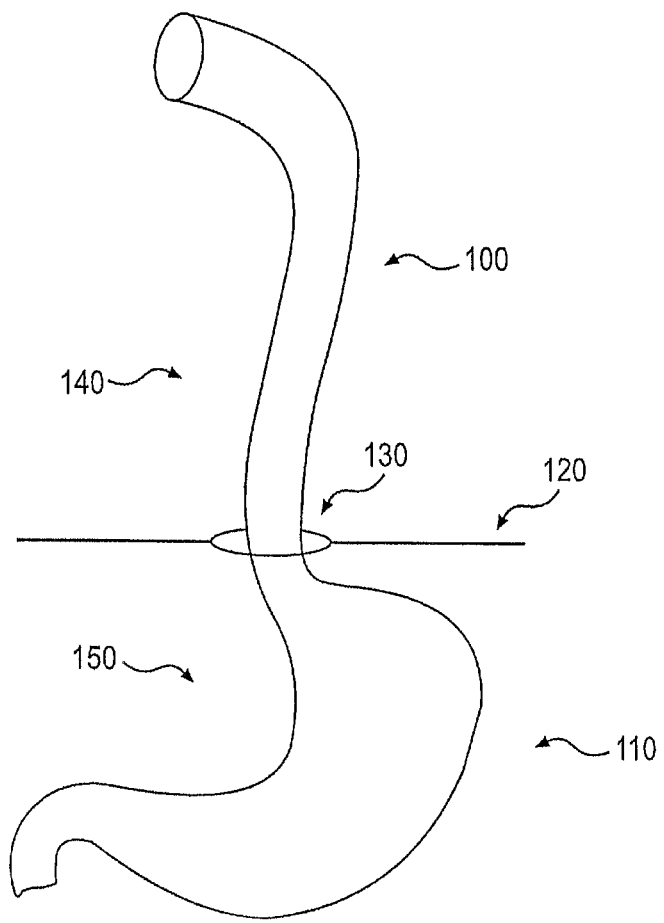
FIG. 8 is a schematic representation of some internal organs of a patient.

FIG. 8 shows a schematic illustration of part of a patient's gastrointestinal tract. An esophagus 100 is shown located above a stomach 110. A diaphragm 120 includes an esophageal hiatus 130, where esophagus 100 passes through diaphragm 120. A mediastinum 140 is located above diaphragm 120 and an abdominal cavity 150 is located below diaphragm 120. Mediastinum 140 includes various other organs not shown in FIG. 8, including the heart and thoracic viscera. Abdominal cavity 150 also includes other organs not shown, such as the liver, vena cava, gallbladder, kidneys, spleen, pancreas, and lower gastrointestinal tract.

Figure 10:
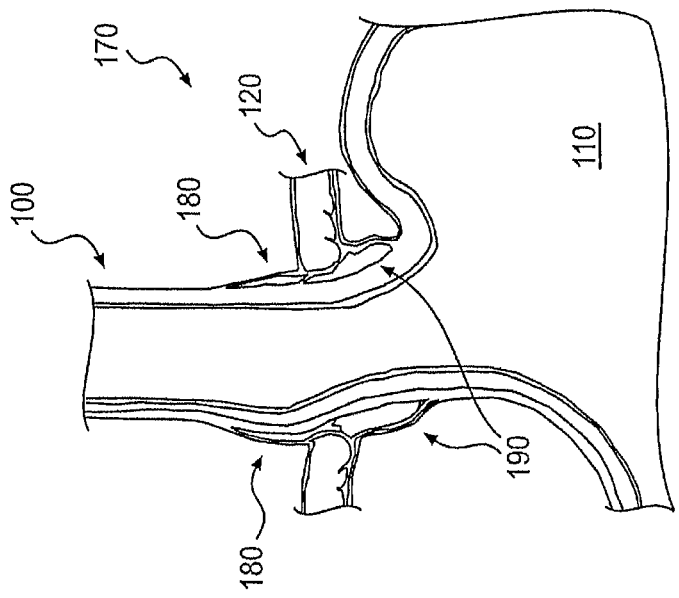
FIG. 10 is a cut-away schematic representation of an esophagogastric junction.
Figure 9:
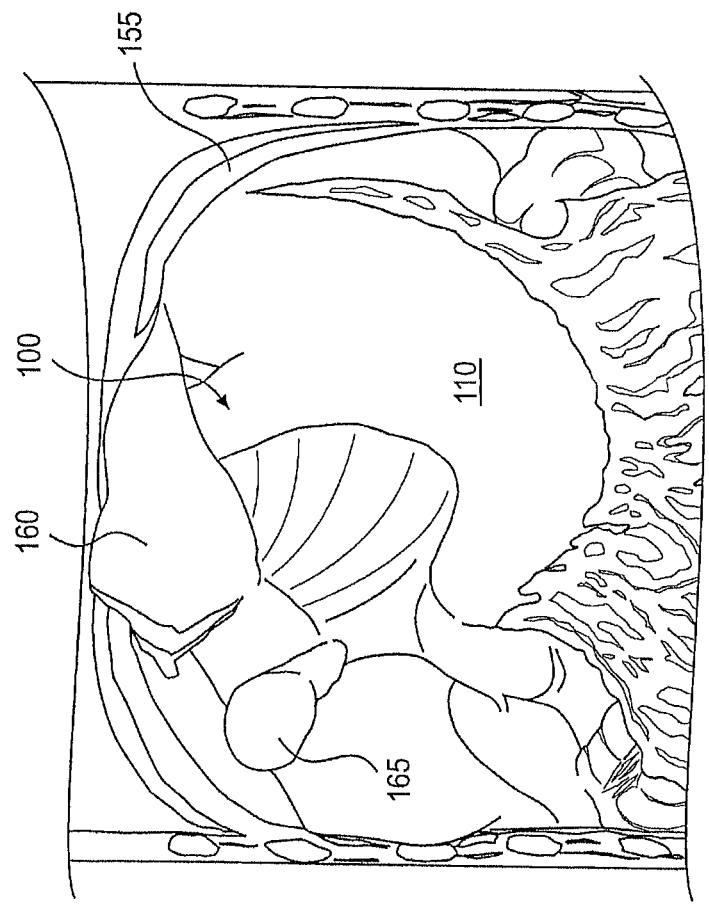
FIG. 9 is a schematic representation of a stomach and surrounding organs in situ.

FIG. 9 shows a liver 160 and a gallbladder 165 partially retracted using an open procedure. Abdominal cavity 150 is surrounded by an abdominal wall 155. As shown in FIG. 9, liver 160 may require partial retraction to gain sufficient access to the gastroesophageal junction 170 (FIG. 10). This may also be required for a minimally invasive procedure. Additionally, at least part of stomach 110 may require mobilization. In some embodiments, mobilization of stomach 110 can be achieved using endoscopic system 10.

FIG. 10 shows a cut away view of esophagogastric junction 170. A phrenoesophageal ligament 180 is shown surrounding a lower part of esophagus 100. A sub-hiatal fat ring 190 is shown inferior to diaphragm 120. Phrenoesophageal ligament 180 can be divided to provide access to mediastinum 140 from abdominal cavity 150.

Figure 11A:
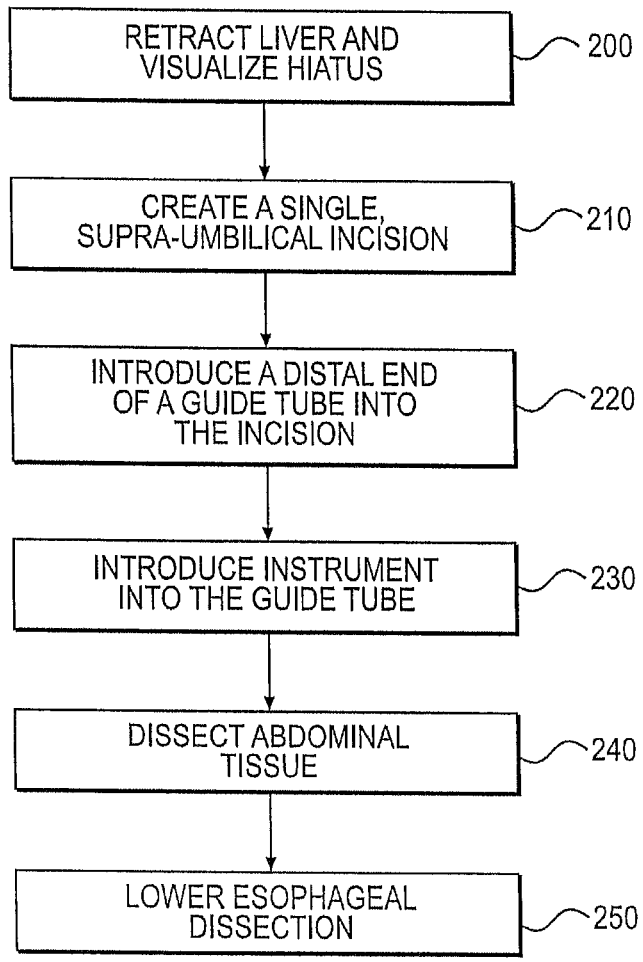
FIG. 11A is a flow chart of a medical procedure, according to an exemplary embodiment.
Figure 11B:
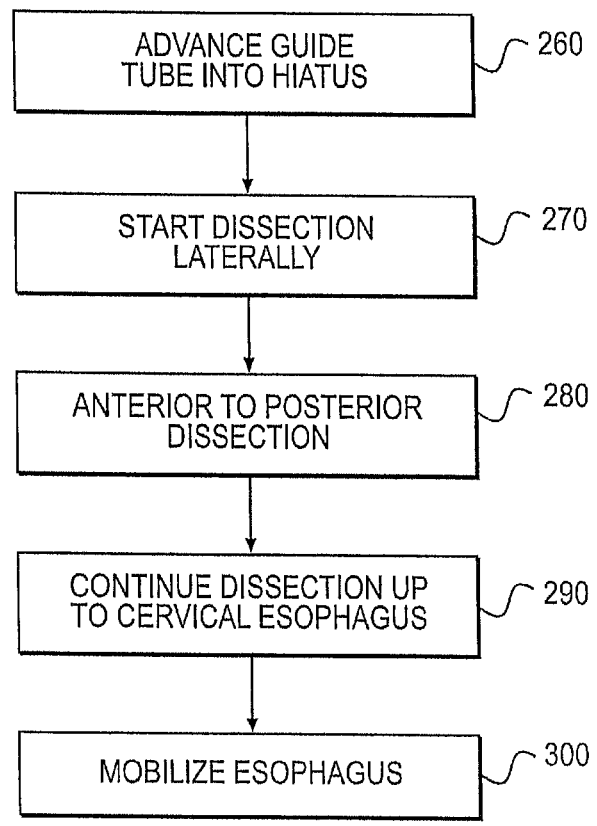
FIG. 11B is a flow chart of a medical procedure, according to an exemplary embodiment.

In accordance with an exemplary embodiment, a medical procedure may be performed as illustrated in the flow charts of FIGS. 11A, 11B. One or more of the steps shown or described herein may be omitted, modified, or repeated as necessary. For example, endoscopic system 10 could be used to perform the medical procedure shown in FIGS. 11A, 11B, or variations thereof. In another embodiment, endoscopic system 10 can be used to provide general access to mediastinum 140 via abdominal cavity 150.

Initially, one or more organs of abdominal cavity 150 may be retracted. In some procedures, one or more laparoscopic devices may be used to retract at least part of one or more organs. Retraction may be necessary to access or visualize esophageal hiatus 130 (Step 200).

Retraction can include various techniques, including using one or more traditional retractors. For example, two trocars may be placed through abdominal wall 155 and positioned to allow partial retraction of liver 160 using two laparoscopic retractors. In other embodiments, endoscopic system 10 could be used to retract one or more organs of the patient. For example, guide tube 20 or instrument 30 may be used in part to retract one or more organs. Because of their flexibility and ability to articulate, guide tube 20 or instrument 30 may be navigated around one or more organs. During such an approach, liver 160 may be retracted via appropriate manipulation of guide tube 20 alone, or in combination with instrument 30 configured to expand or retract tissue.

To assist organ retraction or confirm sufficient access to esophageal hiatus 130, one or more optical devices 40 may be used. As explained above, optical device 40 can include a traditional endoscope, laparoscopic imaging device, or various other types of optical systems. For example, a traditional laparoscopic imaging device (not shown) may be inserted through abdominal wall 155 and positioned to view esophageal hiatus 130. Alternatively, or in combination with the laparoscopic imaging device, one or more optical devices 40 may be located within guide tube 20 and positioned to view esophageal hiatus 130 or another organ within abdominal cavity 150. As such, various imaging systems or modalities could be used with the procedures described herein. Moreover, different imaging systems or modalities could be used at different times throughout the medical procedure.

In some embodiments, a single incision can be created (Step 210). The incision may be formed in abdominal wall 155, and more specifically, through an anterior surface of abdominal wall 155. The incision may be sub-xiphoid, including, for example, through the umbilicus. The purpose of the incision is to permit access to abdominal cavity 150 using guide tube 20. The single incision could replace two, three, or more incisions used during standard laparoscopic procedures.

Distal region 22 of guide tube 20 can be inserted through the incision (Step 220). Then, one or more instruments 30 or optical devices 40 may be located within guide tube 20 (Step 230). It may also be possible to locate instruments 30 or optical device 40 within guide tube 20 prior to inserting guide tube 20 into abdominal cavity 150.

Guide tube 20, instrument 30, and optical device 40 may be configured to be at least partially inserted into an anatomic opening. Guide tube 20, instrument 30, and optical device 40 may be advanced together through tissue. Guide tube 20, instrument 30, and optical device 40 may also be advanced separately in various combinations as each component can be moved independent of movement of one or more other components. For example, guide tube 20 may be advanced along with optical device 40 while one or more instruments 30 remain fixed relative to the patient.

During a procedure, one or more instrument 30 or optical device 40 can be readily removed from guide tube 20 and quickly replaced with another or a different component. The ability to precisely and quickly reposition a component at the surgical site allows a surgeon to quickly respond to unexpected events. For example, grasper 37a and dissector 37b can be quickly replaced with electrocautery hook 37d and suction tube 37e to treat a ruptured blood vessel.

Another advantage of endoscopic system 10 can be the reduced need for insufflation during tissue dissection. That is, one or more components of endoscopic system 10 can dissect tissue without concurrent insufflation of the tissue using pressurized gas. Reducing the need for insufflation can reduce patient pain and recovery time.

To create and navigate a pathway through abdominal cavity 150, various combinations of instrument 30, optical device 40, and guide tube 20 may be used to dissect tissue. For example, distal end 29 of guide tube 20 may be rounded and configured to separate tissue. Optical device 40 could also be used in some capacity to dissect or retract tissue. One or more instruments 30 can be configured to cut, dissect, remove, or ablate tissue. For example, a dissector, scissors, or an electrocautery hook may be used to, respectively, dissect, cut, or ablate tissue.

To dissect tissue in abdominal cavity 150 (Step 240), guide tube 20 may be used. In some embodiments, guide tube 20 can be selectively moved relative to the patient to dissect tissue. Select movement can include moving guide tube 20 relative to platform 50 over relatively small distances, such as, for example, less than one inch. Moving platform 50 relative to the patient can include relatively large distance, such as, for example, advancing guide tube 20 several inches.

Movement over different relative scales can be combined with locked, free, incremental, or other types of select movement to provide improved dissection using endoscopic system 10. As such, the surgeon can precisely control dissection through small-scale and large-scale movement as endoscopic system 10 is progressively repositioned relative to the patient. The surgeon may also freely or incrementally move endoscopic system 10, or lock its position, during the procedure.

In use, a surgeon could initially position endoscopic system 10 relative to the patient. Once suitably positioned, platform 50 could be locked in a first position relative to the patient by, for example, mounting system 60. Then, the surgeon could operate slide assembly 70 to precisely move guide tube 20 relative to the patient and mounting system 60 from the first position to a second position superior to the first position. If necessary, endoscopic system 10 could be re-locked at the superior second position. The surgeon may be able to take his/her hands off one or more components of endoscopic system 10 to reposition another component or perform another task. For example, with guide tube 20 temporarily locked, bleeding vessels may be ligated or fine tissue dissection may be conducted using one or more instruments 30.

Such small-scale, large-scale, free, locked, or incremental control over the movement of endoscopic system 10 can be used to dissect tissue generally not requiring fine dissection. In general, instruments 30 can be used to perform fine dissection of, for example, nerves, vessels, or lymphatic ducts. Abdominal tissue may be dissected using a combination of guide tube 20 and instrument 30.

As described above, one or more different types of instruments 30 can be used in conjunction with endoscopic system 10. For example, a dissector and an electrocautery device can be used to dissect abdominal tissue and seal unwanted perforations to abdominal tissue. Alternatively, or in combination, a balloon dissector or other type of dissector may be used to create space between adjacent intra-abdominal organs.

Once endoscopic system 10 has been navigated through abdominal cavity 150 to a location near esophageal hiatus 130, optical device 40 can be positioned to visualize esophageal hiatus 130. One or more instruments 30 can then be used to dissect at least part of a lower region of esophagus 100 from diaphragm 120 (Step 250). For example, phrenoesophageal ligament 180 can be at least partially divided circumferentially or gastroesophageal junction 170 may be at least partially mobilized.

In general, one or more instruments 30 can be used to divide phrenoesophageal ligament 180 or mobilize gastroesophageal junction 170. Guide tube 20 may be articulated to provide sufficient access to phrenoesophageal ligament 180 or gastroesophageal junction 170. In addition, instrument 30 or optical device 40 may be articulated or repositioned to better access regions of tissue requiring dissection. The order of performing these and other dissection steps may be varied as required. The aim of these steps is to detach the lower region of esophagus 100 from the surrounding tissue and to provide access to mediastinum 140 via esophageal hiatus 130.

Once esophageal hiatus 130 has been sufficiently accessed, one or more components of endoscopic system 10 may be passed through esophageal hiatus 130. In some embodiments, distal tip 29 of guide tube 20 may be passed through esophageal hiatus 130 to enter mediastinum 140 (Step 260). Distal region 32 of instrument 30 may also be passed through esophageal hiatus 130 and into mediastinum 140. Optical device 40 can also be located within mediastinum 140 to better visualize surrounding tissue. If necessary, diaphragm 120 may be partially dissected to provide additional space to pass one or more components through esophageal hiatus 130.

Endoscopic system 10 can permit significant improvement in performing dissections within mediastinum 140 because of improvements in visualization, ergonomics, and fine dissection offered by instruments 30. For example, an extended mediastinal lymphadenectomy was performed significantly more efficiently and effectively using endoscopic system 10 than standard laparoscopic devices. Unlike previous techniques, vagus and recurrent laryngeal nerves can be readily identified and preserved, and perihilar vital structures can be readily observed.

Once inside mediastinum 140, one or more components of endoscopic system 10 may be used to dissect esophagus 100 from the surrounding tissue as previously described. In some embodiments, dissection of esophagus 100 can be conducted laterally (Step 270). Tissue can be dissected left and right about an outer surface of esophagus 100. For example, one or more instruments 30 can be used for fine dissection to precisely cut, separate, ablate, or remove tissue from the periphery of esophagus 100. The dissection can also be carried laterally and anteriorly at the pleural and pericardial margins. If guide tube 20 is located generally anterior to esophagus 100, instruments 30 can be used for anterior to posterior dissection (Step 280).

Figure 12:
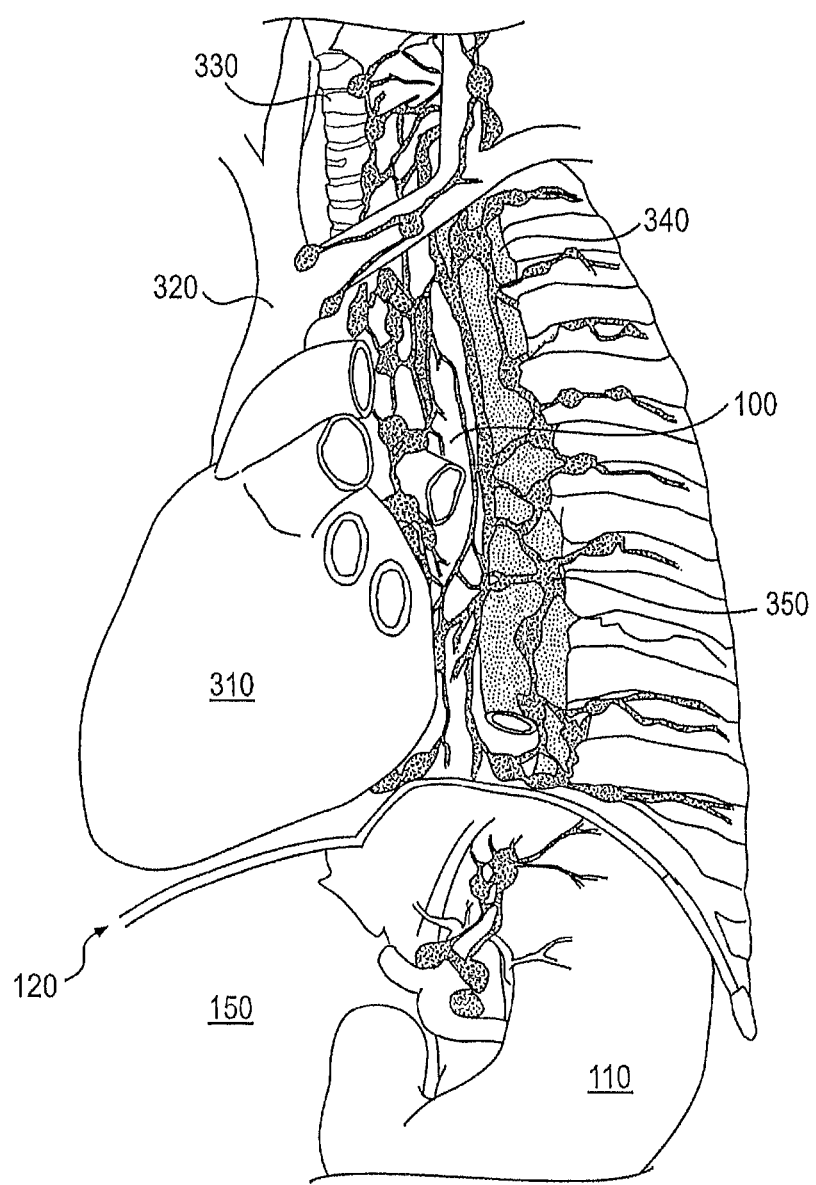
FIG. 12 is a partial cut-away schematic representation of a mediastinum showing cardiac and lymphatic structures.

As shown in FIG. 12, care should be taken to avoid unnecessary disruption of cardiac tissue 310, blood vessels 320, nerves (not shown), trachea 330, spinal cord 340, lymphatic tissue 350, and other organs located adjacent to esophagus 100. Endoscopic system 10 can also be used to divide the mediastinal pleura along the azygos vein (not shown). Lymphatic tissue 350 may be mobilized medially from the azygos vein across the aorta (not shown) in an en bloc fashion to mobilize a posterior region of esophagus 100. Airway structures can also be skeletonized.

Various tissue surrounding esophagus 100 can be separated so as to remove or leave intact the various tissue. For example, some lymphatic tissue 350 on esophagus 100 may be cancerous. Such tissue could be left in contact with esophagus 100 and excised as part of the esophagectomy. For example, subcarinal lymph nodes can be included in the resection margin. Other benign tissue could be separated from esophagus 100, leaving it intact following removal of esophagus 100.

Once a lower region of esophagus 100 is sufficiently dissected, the dissection process can proceed superiorly up towards a cervical region of esophagus 100 (Step 290). These general dissection methods can be repeated until a sufficient length of esophagus 100 has been mobilized (Step 300). If required, endoscopic system 10 could be used to create an internal cervical incision.

In other embodiments, it may be possible to make a superior incision and move endoscopic system 10 interior to reach esophagus 100. For example, an incision could be made in the neck, mouth, or other location superior to mediastinum 140.

Access to mediastinum 140 could then be interior, which may allow for an easier or more efficient approach to esophagus 100 or a proximal organ.

The methods and systems described herein could also be used for therapeutic applications. For example, accessing esophagus 100 may form part of staging a cancer treatment. Once access to mediastinum 140 is achieved, various cancer treatments could be applied using system 10 or other devices. Treatment could be applied to treat esophagus 100, a lung, GI tract, or other organ.

The present system can also maintain improved visualization of target organs compared with traditional techniques. Visualization can be difficult to maintain with traditional devices due to their inflexibility, lack of appropriate articulation, or other limitations. In contrast, endoscopic system 10 can provide improved flexibility and articulation to maintain sufficient visualization of the target organs. For example, endoscopic system 10 can be independently operated while insufflation or retraction is maintained using other devices. Decoupling instrument control from other devices used to maintain an operating space can free a surgeon to focus more on the tissue manipulation required, rather than maintaining tissue access. As such, endoscopic system 10 can accommodate a team of surgeons, increasing the speed, accuracy, or precision of a surgical procedure.

Various other surgical steps may be required during the procedures described herein or similar operations. For example, division of major blood supply may be needed to reduce blood loss during an operation. Clips, ablative energy, ligation, or other devices or methods may be used to limit unwanted bleeding. Various imaging, space creation, closure, or other steps may also be needed based on the type of procedure.

It will be apparent to those skilled in the art that various modifications and variations can be made in the disclosed devices and methods without departing from the scope of the invention. For example, other procedures could be performed based on hiatal access to mediastinum. Some other procedures could include mediastinal node dissection for cancer staging, en bloc esophageal mobilization, excision of benign esophageal lesions, and diverticuli resection, and posterior mediastinal tumor resection. Other embodiments of the invention will be apparent to those skilled in the art from consideration of the specification and practice of the invention disclosed herein. It is intended that the specification and examples be considered as exemplary only.

What is claimed is:

1. A method of performing a medical procedure in a patient, the method comprising:
    creating an incision in the patient;
    inserting a flexible guide tube into the incision;
    advancing a flexible instrument through the guide tube;
    positioning a distal tip of the guide tube adjacent to a gastroesophageal junction;
    passing the instrument through an esophageal hiatus; and
    retracting a liver of the patient to visualize the gastroesophageal junction.

2. The method of claim 1, further including passing the distal tip of the guide tube through the esophageal hiatus and dissecting at least part of an esophagus from the gastroesophageal junction to a cervical region of the esophagus.

3. The method of claim 1, further including mobilizing the gastroesophageal junction.

4. The method of claim 1, further including dividing circumferentially a phrenoesophageal ligament.

5. The method of claim 2, wherein dissecting includes starting a dissection laterally and includes anterior to posterior dissection.

6. The method of claim 1, further including dilating the esophageal hiatus.

7. The method of claim 1, further including accessing at least part of an esophagus by dissecting tissue surrounding the at least part of the esophagus.

8. The method of claim 1, further including positioning a platform relative to the patient, wherein the platform is fixedly positioned relative to the patient, fixedly coupled to the guide tube, and configured to permit selective movement of the guide tube relative to the patient.

9. The method of claim 8, wherein the platform includes a mounting system configured to permit free and locked movement between the guide tube and the patient, and a sliding assembly configured to permit incremental movement between the guide tube and the patient.

10. A method of performing a medical procedure in a patient, the method comprising:
    creating an incision in the patient;
    passing a distal tip of a flexible guide tube through the incision;
    locating a flexible optical device and a flexible instrument within the guide tube;
    retracting at least part of an organ to create a pathway from the incision to an esophageal hiatus;
    advancing the distal tip of the guide tube along the pathway to the esophageal hiatus;
    positioning the optical device to visualize a phrenoesophageal ligament;
    dividing the phrenoesophageal ligament using the instrument; and
    passing at least one of the guide tube, the optical device, and the instrument through the esophageal hiatus.

11. The method of claim 10, wherein the incision is a single incision.

12. The method of claim 10, further including dissecting at least part of an esophagus from tissue surrounding the esophagus.

13. A method of performing a medical procedure in a patient, the method comprising:
    creating an incision in the patient;
    passing a distal end of a flexible guide tube and a distal end of a flexible instrument through the incision;
    creating a pathway from the incision to an esophageal hiatus using at least one of the guide tube and the instrument;
    positioning an optical device to visualize the esophageal hiatus;
    dilating the esophageal hiatus using the instrument;
    passing the instrument through the esophageal hiatus and into a mediastinum; and
    passing the guide tube through the esophageal hiatus and into the mediastinum.

14. The method of claim 13, further including dissecting an esophagus from a gastroesophageal junction to a cervical esophagus.

15. The method of claim 13, further including removing a lymph node from the mediastinum.

16. The method of claim 1, wherein the incision is in an abdominal wall of the patient.

17. The method of claim 10, wherein the incision is in an abdominal wall of the patient.

18. The method of claim 13, wherein the incision is in an abdominal wall of the patient.

19. The method of claim 1, wherein the instrument is a retractor.

20. The method of claim 13, wherein the guide tube is attached to a mounting system, and the method further includes locking the mounting system in a position relative to the patient.

* * * * *